(12) United States Patent
Hassan

(10) Patent No.: US 6,521,243 B2
(45) Date of Patent: Feb. 18, 2003

(54) IONIC CHITOSAN -IODINE COMPLEXES: ANTISEPTIC HYDROGELS AND WOUND HEALING PROMOTERS

(75) Inventor: EmadEldin M. Hassan, Philadelphia, PA (US)

(73) Assignee: Pharma C and D, Limited, Nicosia (CY)

( * ) Notice: Subject to any disclaimer, the term of this patent is extended or adjusted under 35 U.S.C. 154(b) by 0 days.

(21) Appl. No.: 09/748,335

(22) Filed: Dec. 22, 2000

(65) Prior Publication Data

US 2002/0119205 A1 Aug. 29, 2002

(51) Int. Cl.$^7$ .......................... A01N 25/34; A61K 33/18
(52) U.S. Cl. ........................ 424/404; 424/669; 424/667
(58) Field of Search .......................... 424/404, 76, 150, 424/180, 669, 667, 488; 514/55

(56) References Cited

U.S. PATENT DOCUMENTS 5,538,955 A * 7/1996 De Rosa et al. .............. 514/55

OTHER PUBLICATIONS

Kramer, Sheila A., "Effect of povidone–iodine on wound healing: A review." Journal of Vascular Nursing 1999; vol. 17, No. 1: 17–23.

Kashyap, Ajaya., "Effect of Povidone Iodine Dermatologic Ointment on Wound Healing." Am. Surgery 1995; 61(6) 486–491.

Kratz, Gunnar, et al., "Heparin–Chitosan Complexes Stimulate Wound Healing in Human Skin." Scandinavian University Press 1997; 31: 119–123.

Takeuchi, Hirofumi, et al., "Spray–Dried Lactose Composite Particles Containing an Ion Complex of Alginate–Chitosan for Designing a Dry–Coated Tablet Having a Time–Controled Releasing Function." Pharmaceutical Research 2000; vol. 17, No. 1: 94–99.

Muzzarelli, Riccardo A. A., et al., "Biochemistry, histology and clinical uses of chitins and chitosans in wound healing." Birkhauser Verlag Basel/Switzerland 1999: 251–263.

Shu, X. Z., and K. J. Zhu, "A novel approach to prepare tripolyphosphate/chitosan complex beads for controlled release drug delivery." International Journal of Pharmaceutics 2000, 201: 51–58.

Hassan, Emad E., and James M. Gallo. "Targeting Anticancer Drugs to the Brain. I: Enhanced Brain Delivery of Oxantrazole following Administration in Magnetic Cationic Microspheres." Journal of Drug Targeting 1993; 1: 7–14.

Hassan, Emad E., and James M. Gallo. "A Simple Rheological Method for the in Vitro Assessment of Mucin–Polymer Bioadhesive Bond Strength." Pharmaceutical Research 1990; vol. 7, No. 5: 491–495.

* cited by examiner

Primary Examiner—Thurman K. Page
Assistant Examiner—Blessing Fubara
(74) Attorney, Agent, or Firm—Dann, Dorfman, Herrell & Skillman

(57) ABSTRACT

This invention describes non-staining, pharmaceutically useful compositions of ionic complexes made between the cationic polymer chitosan or its derivatives and the small anionic iodine-iodide complex (ICIC's). Unlike previously disclosed ion transfer chitosan iodine complexes, ICIC's were found to possess dramatically higher viscosity than those of each ingredient separately, and instantly form a gel structure that is easily dispersible upon shaking. In addition to their antiseptic power, ICIC's showed better skin biocompatibility than povidone iodine and effectively promoted wound healing.

16 Claims, No Drawings

IONIC CHITOSAN-IODINE COMPLEXES: ANTISEPTIC HYDROGELS AND WOUND HEALING PROMOTERS

FIELD OF THE INVENTION

This invention is related to ionic complexes of iodine with chitosan or its derivatives, methods of preparation thereof and pharmaceutically useful compositions containing these complexes. This invention is also related to hydrogels made of chitosan-iodine ionic complexes. This invention further relates to methods of treatments by these preparations, and their use in promoting wound healing and as antiseptics.

BACKGROUND OF THE INVENTION

Wounds are internal or external bodily injuries or lesions caused by physical, chemical, microbial, or thermal means. Natural wound healing involves a series of three processes:

a. An inflammation phase where platelet aggregation and clotting occur to stop bleeding and induce influx of various types of cells to start a cellular proliferation process;

b. A cellular proliferation phase where new connective or granulation tissue is formed; and c. A remodeling phase where the granulation tissue is replaced by collagen and elastin fibers forming a scar.

The primary step in wound treatment is to prevent or eliminate microbial contamination of wounds by using disinfectants or antiseptics. Since contaminating microbes release toxins and cause pathological changes at the wound site, delaying the natural healing process, the use of antimicrobials is an essential first step in wound treatment.

Among antimicrobials, iodine in its elementary state exhibits a universal germicide activity against bacteria, fungi, and viruses and for this reason has been used in alcoholic solutions for decades. However, the limits to this use are the low stability of iodine solutions, its notable aggressiveness on tissues when applied as a solution, and the persistent staining it leaves on applied tissues.

More recently, water soluble forms of iodine (known as iodophors) have been commercialized which only partially reduced these undesirable side effects. The most common employed iodophor is polyvinylpyrrolidone-iodine, (also known as povidone iodine). Povidone iodine is used for pre-operative skin disinfections, wound disinfections, and as a mouthwash and vaginal antiseptic. However, in wound treatment, povidone iodine does not effectively promote good wound healing. In fact, it either impaired wound healing or reduced wound strength. (Kramer, J. Vasc. Nurs. 1999 March: 17(1) 17–23). In addition, povidone iodine showed negative effects on wound healing, similar to those of steroids (Kashyap et al., Am. Surg. 1995 June; 61(6) 486–491).

A few attempts to prepare iodine-containing compositions to mitigate the adverse effects of both elemental iodine and povidone iodine were made, using chitosan and its derivatives. Chitosan derivatives include, but are not limited to chitin, N-carboxybutylchitosan, N-acylchitosan, N-carboxymethylchitosan, N-O-carboxymethylchitosan and N-O-chitosan sulphate. (See U.S. Pat. Nos.: 4,275,194 and 5,538,955).

Chitosan is a cationic polysaccharide obtained by deacetylation of the natural polymer chitin. Kato et al. (U.S. Pat. No. 4,275,194) have described a process to prepare chitosan iodine adducts for a disinfectant and a deodorant use. The process involved many days of impregnation and drying and the final product was recovered in the form of dry dark brown powder. The mentioned method failed to provide a commercially feasible way for production and use, due to the extensive time periods required for preparation and the inconvenient non-liquid form of the product.

Because chitosan and derivatives have been recognized for their wound healing activity, DeRosa et al. (U.S. Pat. No. 5,538,955) have described different procedures to prepare solid forms of chitosan-iodine products. Those procedures required the use of elevated temperatures, special reactors for hazardous iodine gas, and took up to 5 days to complete. The resultant solid product took one to two days to dissolve in a suitable liquid. DeRosa et al. also suggested a liquid chitosan iodine preparation using high concentrations of surfactants. Because surfactants are known for their ability to dissolve or modify natural cell lipid membranes, they can damage the protective barrier nature of the skin, causing skin tissue destruction and delayed wound healing.

Despite the fact that chitosan iodine products have been proposed for more than twenty years, a clinically and pharmaceutically acceptable liquid formulation is yet to be established. It is the purpose of this invention to disclose a practical, fast and efficient method of preparing chitosan iodine liquid preparations that will eliminate the above mentioned limitations of iodine, povidone iodine and previously disclosed chitosan iodine compositions.

This invention also has superior utility in promoting wound healing without the need of additional medications such as growth factors (Drohan et al, U.S. Pat. No. 6,124,273) or immobilized heparin (Kratz et al., Scand. J. Plast. Reconstr. Surg. Hand Surg. 1997). In the prior art formulations, such medications or supplements were required to overcome the limited efficiency of chitosan when used as a sole wound healing promoter.

SUMMARY OF THE INVENTION

It is the object of this invention to provide liquid chitosan iodine compositions suitable for treatment of wounds by acting as antiseptics and a wound healing promoters. Another object of this invention is the formation of said useful compositions as ionic complexes between positively charged chitosan molecules in solution and the solution of the small anionic iodine-iodide complexes (will be referred to as ionic chitosan iodine complex or ICIC's). A further object of this invention is the preparation of said compositions without the need of heat, special reactors, surfactants or volatile solvents, such as alcohol. A further object of this invention is a composition of ICIC's formulated as a hydrogel and the use thereof to promote wound healing.

DESCRIPTION OF THE INVENTION

In accordance with the present invention, it has been discovered that, unlike previously disclosed iodine based compositions, identified as adducts or charge transfer complexes, ICIC's were found to possess dramatically higher viscosity and instantly form a gel structure that easily disperses upon shaking. A further discovery is that the color of ICIC's is dark purple which is easily distinguished from the dark brown or orange yellow colors of other chitosan iodine complexes. A yet further advantage of this invention is that treatment with the compositions of the invention results in fast wound healing, minimal scar formation. Furthermore, permanent staining of the skin does not occur.

In one embodiment, this invention provides a composition of matter comprising an ionic complex between cationic chitosan molecules in solution and a monovalent, anionic small complex made of iodine-iodide ($I_3^-$). A second embodiment of this invention involves the existence of ICIC in a hydrogel form suitable for direct application to intact or wounded skins of animals or humans. A third embodiment of this invention involves the formation of such complex in a homogeneous hydrogel form, without the need of any additional polymers or thickening agent. A fourth embodiment of this invention involves casting ICIC hydrogel into solid powder or flexible films or otherwise suitable films or sheets or the like.

The pharmaceutical compositions of this invention include, without limitation:
1. Chitosan, or derivative, having an average molecular weight between 10 to 1000 kilo Daltons, preferably in the range of 100–800 kilo Daltons, and most preferably in the range of 250 to 750 kilo Daltons. The degree of deacetylation of chitosan is 40% to 95%, preferably 60% to 90%.
2. An aqueous vehicle that may include:
   a. An acid from the group of acetic, lactic, citric, glycolic, and the like, or their buffers or salts, at a concentration resulting in pH values of the final composition between 3.0 and 8.0, more preferably between 4.0 and 7.0.
   b. A low molecular-weight diol, such as ethylene or propylene glycol, a triol such as glycerol, or a polyol such as sorbitol or polyethylene glycol, at a concentration range between 5% and 25%.
3. Elemental iodine at the concentration range of 0.05% to 5.0%, preferably at the concentration range of 0.1% to 1%.
4. An iodide source such as potassium iodide, sodium iodide, or zinc iodide or the like, at a concentration range of 0.05% to 5%, preferably at a concentration range of 0.1% to 1.0%, or hydroiodic acid of similar concentrations.

In this invention, the low-molecular weight diol, triol, or polyol functions as a "non-volatile" compound. As used herein, the expression "non-volatile" means having a boiling point equal to or greater than the boiling point of ethylene glycol, that is, greater than or equal to 198° C.

It has been discovered that the compounding order of the above composition is very critical and has to be performed so that both the cationic polymer and the iodine-iodide complex are prepared in separate portions of the aqueous vehicle prior to final mixing.

An advantageous feature of this invention is the instant formation of ICIC in a gel form following the mixing of the cationic and anionic components. The formed gel will provide utmost physical stability of the product during storage, yet can easily be transformed into pourable fluid upon gentle shaking. The pourable fluid form has the advantage of easily spreading on wounds or skin without the need of rubbing. Another advantage of this invention is that, once ICIC's stay in contact with tissues, they transform back to a protective flexible film that will protect the wound from the surrounding environments, and slowly release active iodine for disinfecting the tissue.

The formed protective film can also control oxygen permeability to the wound and eliminate the need of using occlusive bandages. The formed film can also prevent the need for frequent wound treatments, which are usually painful. Another advantage of ICIC hydrogel is their ability to be cast and dried into flexible sheets or films that can serve as self-medicated bandages. Such bandage can absorb wound discharge, accelerating wound repair. A further advantage of these dried films is they can be naturally degraded by tissue enzymes without the need to remove them.

The following examples further illustrate the composition and use of this invention and are not intended to be limiting.

EXAMPLE 1

A 100 ml solution of ICIC was made, consisting of:
a. 0.8% chitosan (molecular weight of 650 kilo Daltons, 90% deacetylation degree);
b. 0.8% acetic acid; c. 1% potassium iodide;
d. 1% iodine; and
e. 10% glycerol.

Chitosan was dissolved in acetic acid, while potassium iodide and iodine were dissolved in a separate aqueous medium. Glycerol was then added to the iodine iodide mixture. Finally, chitosan solution was mixed with the iodine containing liquid. The formed composition was a dark purple, highly viscous, structured hydrogel that becomes thin fluid upon shaking.

EXAMPLE 2

A 100 ml solution of ICIC was made, consisting of:
a. 1.8% chitosan (molecular weight 100 Kilo Daltons, 90% deacetylation degree);
b. 1.8% acetic acid;
c. 0.4% potassium iodide;
d. 0.4% iodine.

Chitosan was dissolved in acetic acid, while potassium iodide and iodine were dissolved in a separate aqueous medium. Glycerol was then added to the iodine iodide mixture. Finally, chitosan solution was mixed with the iodine containing liquid. The formed composition was a dark purple, highly viscous, structured hydrogel that becomes thin fluid upon shaking.

The following references, all of which are incorporated herein by reference, are included so that the invention may be more fully understood and practiced. The following references are not intended to be limiting.

REFERENCES

U.S. Patent Documents

| | | |
|---|---|---|
| 5,129,877 | Gallo et al. | Jul 1992 |
| 5,902,798 | Gouda et al. | May 1999 |
| 5,620,706 | Dumitriu et al. | Apr 1997 |
| 5,836,970 | Pendit | Nov 1998 |
| 6,150,581 | Jiang et al. | Nov 2000 |
| 4,275,194 | Kato et al. | Jun 1981 |
| 5,538,955 | DeRosa et al. | Jul 1996 |
| 6,124,273 | Drohan et al. | Sep 2000 |

OTHER REFERENCES

Hassan et al., J. Drug Targeting, 1:7–14, 1993.
Hassan et al., Pharm.Res., 7: 491–495, 1990
Shu et al., Int. J. Pharm., 15:201(1):51–58, 2000
Kramer, J. Vasc. Nurs., 1999 March: 17(1) 17–23
Kashyap et al., Am. Surg., 1995 Jun; 61(6) 486–491
Takeuchi et al., Pharm. Res., 17:94–99, 2ooo
Muzzarelli et al., EXS 1999; 87:251–264
Kratz et al., Scand. J. Plast. Reconstr. Surg. Hand Surg. 1997

I claim:
1. A solution comprising an ionic chitosan iodine complex, said solution consisting essentially of:
   a. chitosan or a derivative thereof selected from the group consisting of chitin, N-carboxybutylchitosan,

N-acylchitosan, N-carboxymethylchitosan, N-O-carboxymethylchitosan and N-O-chitosan sulphate;
b. an aqueous vehicle;
c. elemental iodine; and
d. an iodide source.

2. The solution of claim 1 wherein the chitosan or derivative thereof has a molecular weight of 10 to 100 Kilo Dalton.

3. The solution of claim 1 wherein the chitosan or derivative thereof has a degree of deacetylation of 30% or more.

4. The solution of claim 1 wherein the aqueous vehicle includes at least one acid selected from the group consisting of: acetic acid, lactic acid, citric acid, glycolic acid, and a buffer or salt thereof.

5. The solution of claim 4 having a pH value between 3.0 and 8.0.

6. The solution of claim 1 wherein the chitosan iodide complex further comprises a non-volatile compound containing two or more hydroxyl groups.

7. The solution of claim 6 wherein the non-volatile compound is from the group of ethylene glycol, propylene glycol, glycerol, sorbitol or polyethylene glycol, or the like, at a concentration range between 5% and 25%.

8. The solution of claim 1 wherein the concentration range of the elemental iodine is 0.05% to 1%.

9. The solution of claim 1 wherein the iodide source is selected from the group consisting of hydroiodic acid, potassium iodide and sodium iodide.

10. The solution of claim 1 wherein the iodide source is present at a concentration range of 0.05% to 1%.

11. The solution of claim 1, wherein said solution is a pharmaceutical hydrogel.

12. The solution of claim 1, wherein said hydrogel is applied to wounds.

13. The solution of claim 1, wherein said hydrogel promotes wound healing.

14. The solution of claim 1, wherein said hydrogel is a disinfectant for skin, body surfaces and body cavities.

15. The solution of claim 1, wherein the hydrogel is incorporated into bandages, films or sutures.

16. A method for making an iodine chitosan complex, said method comprising the steps of:
a. dissolving chitosan or a derivative thereof selected from the group consisting of chitin, N-carboxybutylchitosan, N-acylchitosan, N-carboxymethylchitosan, N-O-carboxymethylchitosan and N-O-chitosan sulphate in a portion of an aqueous vehicle to maintain or acquire positive charge;
b. dissolving iodine and an iodide source in a second portion of aqueous vehicle to maintain or acquire a negative charge; and
c. mixing the two portions of aqueous vehicle to form a homogeneous composition.

* * * * *